US007749185B2

(12) United States Patent
Wilson et al.

(10) Patent No.: US 7,749,185 B2
(45) Date of Patent: *Jul. 6, 2010

(54) METHOD OF INSERTING DOUBLE-Y-SHAPED CATHETER WITH ATTACHABLE HUBS

(76) Inventors: Jon S. Wilson, 965 Avon Rd., Winston-Salem, NC (US) 27104; Carl M. Fleming, 953 SE. MacArthur Blvd., Stuart, FL (US) 34996; Kenneth T. Cassidy, 866 Farmington Rd., Mocksville, NC (US) 27028; Ronald D. Boyd, 1912 W. Hampton Point, Statesboro, GA (US) 30458; Gary S. Fleming, 428 SW. Squire Johns La., Palm City, FL (US) 34990

(*) Notice: Subject to any disclaimer, the term of this patent is extended or adjusted under 35 U.S.C. 154(b) by 1265 days.

This patent is subject to a terminal disclaimer.

(21) Appl. No.: 10/796,495

(22) Filed: Mar. 9, 2004

(65) Prior Publication Data

US 2004/0172003 A1 Sep. 2, 2004

Related U.S. Application Data

(63) Continuation of application No. 10/231,748, filed on Aug. 30, 2002, now Pat. No. 6,872,198, which is a continuation-in-part of application No. 10/086,033, filed on Feb. 28, 2002, now Pat. No. 6,638,242, which is a continuation of application No. 09/769,052, filed on Jan. 24, 2001, now abandoned.

(51) Int. Cl.
*A61M 3/00* (2006.01)

(52) U.S. Cl. ............... 604/43; 604/164.01; 604/164.1; 604/170.02; 604/271; 604/544; 604/28; 604/508

(58) Field of Classification Search ............ 604/513, 604/523, 533–535, 537–539, 284, 264, 913, 604/500, 506–508, 104, 93.01, 158, 164.01, 604/164.03, 164.04, 164.09–164.11, 170.01, 604/170.02, 174, 175, 43, 271, 544, 28

See application file for complete search history.

(56) References Cited

U.S. PATENT DOCUMENTS 4,134,402 A 1/1979 Mahurkar (Continued)

FOREIGN PATENT DOCUMENTS

EP 0 453 234 A 10/1991
WO WO 9722374 6/1997

OTHER PUBLICATIONS

Complaint from *Arrow International, Inc., et al. v. Spire Biomedical, Inc.* asserting U.S. Patent No. 6,872,198 which shares common "Related U.S. Applications" with the present application, i.e. U.S. Appl. No. 10/086,033, now U.S. Patent No. 6,638,242, and U.S. Appl. No. 09/769,092, now abandoned.

(Continued)

*Primary Examiner*—Nicholas D Lucchesi
*Assistant Examiner*—Quynh-Nhu H Vu
(74) *Attorney, Agent, or Firm*—Amster, Rothstein & Ebenstein LLP (57) ABSTRACT

A method for inserting a multi-lumen catheter into a patient is disclosed. The catheter includes an elongated, central, multi-lumen tube portion having a proximal end and a distal end. A distal branch portion includes a plurality of single-lumen distal extension tubes. The proximal first end of each distal extension tube is connected to the distal end of the central tube portion such that the single lumen of each distal extension tube is in fluid communication with one of the plurality of lumens of the central tube portion. A proximal branch portion includes a plurality of single-lumen proximal extension tubes. The distal first end of each proximal extension tube is connected to the proximal end of the central tube portion such that the single lumen of each distal extension tube is in fluid communication with one of the plurality of lumens of the central tube portion. Each lumen of the central tube portion and the lumens of the distal and proximal extension tubes in fluid communication therewith define a flow path through the catheter. Selectively attachable hub connectors are provided for selective attachment to the distal extension tubes and connection of the catheter to a fluid exchange device.

23 Claims, 10 Drawing Sheets

U.S. PATENT DOCUMENTS

| | | | |
|---|---|---|---|
| 4,299,228 A | 11/1981 | Peters | |
| 4,327,722 A | 5/1982 | Groshong et al. | |
| 4,432,752 A * | 2/1984 | Marlon | 604/500 |
| 4,453,928 A | 6/1984 | Steiger | |
| RE31,873 E | 4/1985 | Howes | |
| 4,543,087 A | 9/1985 | Sommercorn et al. | |
| 4,568,329 A | 2/1986 | Mahurkar | |
| 4,619,643 A | 10/1986 | Bai | |
| 4,623,327 A | 11/1986 | Mahurkar | |
| 4,643,711 A | 2/1987 | Bates | |
| 4,675,004 A | 6/1987 | Hadford et al. | |
| 4,681,122 A | 7/1987 | Winters et al. | |
| 4,682,978 A | 7/1987 | Martin | |
| 4,692,141 A | 9/1987 | Mahurkar | |
| 4,772,268 A | 9/1988 | Bates | |
| 4,772,269 A | 9/1988 | Twardowski | |
| 4,808,155 A | 2/1989 | Mahurkar | |
| 4,832,687 A * | 5/1989 | Smith, III | 604/506 |
| 4,895,561 A | 1/1990 | Mahurkar | |
| 5,053,003 A | 10/1991 | Dadson et al. | |
| 5,053,004 A | 10/1991 | Markel et al. | |
| 5,053,023 A | 10/1991 | Martin | |
| 5,059,170 A | 10/1991 | Cameron | |
| 5,106,368 A | 4/1992 | Uldall et al. | |
| 5,129,891 A | 7/1992 | Young | |
| 5,171,227 A | 12/1992 | Twardowski | |
| 5,190,520 A | 3/1993 | Fenton, Jr. et al. | |
| 5,312,337 A | 5/1994 | Flaherty et al. | |
| 5,334,185 A | 8/1994 | Giesy et al. | |
| 5,342,386 A | 8/1994 | Trotta | |
| 5,360,397 A | 11/1994 | Pinchuk | |
| 5,380,276 A | 1/1995 | Miller et al. | |
| 5,399,168 A | 3/1995 | Wadsworth, Jr. et al. | |
| 5,417,668 A | 5/1995 | Setzer et al. | |
| 5,423,768 A | 6/1995 | Folden et al. | |
| 5,431,661 A | 7/1995 | Koch | |
| 5,472,432 A | 12/1995 | Martin | |
| 5,509,897 A | 4/1996 | Twardowski et al. | |
| 5,558,635 A | 9/1996 | Cannon | |
| 5,599,328 A | 2/1997 | Stevens | |
| 5,624,413 A * | 4/1997 | Markel et al. | 604/523 |
| 5,632,729 A | 5/1997 | Cai et al. | |
| 5,637,102 A | 6/1997 | Tolkoff et al. | |
| 5,685,867 A | 11/1997 | Twardowski | |
| 5,704,915 A | 1/1998 | Melsky et al. | |
| 5,718,678 A | 2/1998 | Fleming, III | |
| 5,743,873 A | 4/1998 | Cai et al. | |
| 5,772,643 A | 6/1998 | Howell et al. | |
| 5,776,111 A | 7/1998 | Tesio | |
| 5,797,869 A | 8/1998 | Martin | |
| 5,807,311 A | 9/1998 | Palestrant | |
| 5,876,366 A | 3/1999 | Dykstra et al. | |
| 5,944,732 A | 8/1999 | Raulerson et al. | |
| 5,947,953 A | 9/1999 | Ash et al. | |
| 5,989,206 A | 11/1999 | Prosl et al. | |
| 5,989,213 A | 11/1999 | Maginot | |
| 6,001,079 A * | 12/1999 | Pourchez | 604/43 |
| 6,033,382 A | 3/2000 | Basta | |
| 6,074,374 A | 6/2000 | Fulton | |
| 6,086,555 A | 7/2000 | Eliasen et al. | |
| 6,113,572 A | 9/2000 | Gailey et al. | |
| 6,156,016 A | 12/2000 | Maginot | |
| 6,190,349 B1 | 2/2001 | Ash et al. | |
| 6,190,371 B1 | 2/2001 | Maginot | |
| 6,206,849 B1 | 3/2001 | Martin et al. | |
| 6,293,927 B1 * | 9/2001 | McGuckin, Jr. | 604/266 |
| 6,342,120 B1 | 1/2002 | Basta | |
| 6,428,513 B1 | 8/2002 | Abrahamson | |
| 6,585,705 B1 | 7/2003 | Maginot et al. | |
| 6,638,242 B2 * | 10/2003 | Wilson et al. | 604/43 |
| 6,682,498 B2 | 1/2004 | Ross | |
| 6,682,519 B1 | 1/2004 | Schon | |
| 6,695,832 B2 | 2/2004 | Schon et al. | |
| 6,749,574 B2 | 6/2004 | O'Keefe | |
| 6,872,198 B1 * | 3/2005 | Wilson et al. | 604/513 |
| 6,921,396 B1 * | 7/2005 | Wilson et al. | 604/508 |
| 2001/0041857 A1 | 11/2001 | Sansoucy | |
| 2003/0088213 A1 | 5/2003 | Schweikert et al. | |
| 2003/0153898 A1 | 8/2003 | Schon et al. | |
| 2004/0065333 A1* | 4/2004 | Wilson et al. | 128/898 |

OTHER PUBLICATIONS

Instructions for Use (Copyright Dated 1990) for Polycath Polyurethane Central Venous Catheter; believed to have been packaged with product believed to have been sold in the United States before Jan. 2000 and related marketing materials.

Instructions for Use (Copyright Dated 1992) for FloLock Single Lumen Bi-directional Valved Catheter; believed to have been packaged with product believed to have been sold in the United States before Jan. 2000.

Instructions for Use (not dated) for Infuse-a-Cath Polyurethane Central Venous Catheter; believed to have been packaged with product believed to have been sold in the United States before Jan. 2000.

Pictures of device believed to be partial sample of a product believed to have been sold in the United States before Jan. 2000 with the Polycath and/or Infuse-a-Cath Instructions for Use.

Copending U.S. Appl. No. 10/251,411; entitled Multi-Lumen Catheter with Attacheble Hub, filed Sep. 20, 2002.

Copending U.S. Appl. No. 10/231,577; entitled Multi-Lumen Catheter with Integrated Connector, filed Aug. 30, 2002.

Copending U.S. Appl. No. 10/231,748; Double Y-Shaped Multi-Lumen Catheter with Selectively Attachable Hubs, filed Aug. 30, 2002.

Copending U.S. Appl. No. 10/612,532; entitled Multi-Lumen Catheter with Attachable Hub, filed Jul. 1, 2003.

Abandoned U.S. Appl. No. 10/086,033; entitled Multi-Lumen Catheter with Attacheble Hub, filed Jan. 24, 2001.

Instructions For Use For Diatek Cannon Catheter Product First Sold in the United States, Sep. 2001.

Supplementary European Search Report dated May 8, 2008 for EP 03 79 1935.

* cited by examiner

METHOD OF INSERTING DOUBLE-Y-SHAPED CATHETER WITH ATTACHABLE HUBS

RELATED APPLICATIONS

This application is a continuation of U.S. patent application Ser. No. 10/231,748 filed Aug. 30, 2002, now U.S. Pat. No. 6,872,198 which is a continuation-in-part of U.S. patent application Ser. No. 10/086,033, filed Feb. 28, 2002, now U.S. Pat. No. 6,638,242, which is a continuation of U.S. patent application Ser. No. 09/769,052, filed Jan. 24, 2001, abandoned.

BACKGROUND

1. Field of the Invention

The present invention relates generally to medical instrumentation and more specifically to a multi-lumen catheter including y-shaped distal and proximal ends, and including selectively attachable hubs for selectively connecting the catheter to a fluid exchange device.

2. Description of the Prior Art

Catheters, generally, are hollow, flexible tubes for insertion into a body cavity, duct, or vessel to allow the passage of fluids or distend a passageway. Catheters are often used for temporary or long-term dialysis treatment. Dialysis treatment provides for blood to be withdrawn from the patient, purified, and then returned to the patient. Thus, in dialysis treatment, catheters are used to allow passage of a patient's blood into and out of the patient's body. For optimal performance during dialysis treatment, the catheter tips, both in-flow and out-flow, should be placed in close proximity to the heart. Typically, medical personnel use either a double lumen catheter or two single lumen catheters. Both types, however, present certain deficiencies.

While double lumen catheters (e.g., U.S. Pat. No. 4,895,561) allow for a single insertion of the catheter into the desired vein, double lumen catheters typically do not permit optimal catheter tip placement. Due to differences among patients, optimal tip position varies from patient to patient. Non-optimal tip position may significantly lower flow values, resulting in less effective dialysis treatment. For current double lumen catheters, a physician must make an estimate regarding the appropriate catheter tube length prior to beginning the procedure of catheterization. Then, a subcutaneous tunnel is made from a first end, which is near the area to be catheterized, to a second end, which is the preferred end position of the hub assembly, namely, away from the neck of the patient, in order to allow for more convenient access to the dialysis treatment equipment. The catheter tube is then routed forwardly through the subcutaneous tunnel from the second end to the first end so that the catheter tips extend outwardly from the first end of the tunnel. Either before or after tunneling, a sheath is inserted through the first end of the tunnel and into the area to be catheterized, and the catheter tips are inserted into the sheath and the area to be catheterized. The estimated catheter tube length and subsequent forward tunneling may result in less than optimal tip placement.

With the use of two independent single lumen catheters (e.g., U.S. Pat. No. 5,776,111 to Tesio) the problem of tip placement is addressed. The hub assembly of each catheter is removable from the tube and tip portion of the catheter, thereby allowing the catheter tip to be placed directly into the vein and advanced into the desired position. Then, the proximal end of the catheter can be reverse tunneled and trimmed to a desired length. Thereafter, the hub assembly is attached. Deficiencies, however, exist in this method of catheterization as well. One problem associated with this method is that this method requires two separate venous insertions, namely, two tunnels and two of each accessory instrument used for the procedure. Therefore, there is increased surgical time required to place two catheters, there are two wound entry sites which doubles the risk of post-surgical infection, and the two catheters together are significantly larger in diameter than one double lumen catheter.

Applicant's co-pending application Ser. No. 09/769,052, filed Jan. 24, 2001, and Ser. No. 10/086,033, filed Feb. 28, 2002, disclose a multi-lumen catheter apparatus and method for inserting the apparatus in a patient. The disclosures of these co-pending applications are hereby incorporated by reference. In the disclosed apparatus and method, a multi-lumen catheter includes a selectively attachable hub assembly that allows the catheter tip to be positioned accurately within a patient's vein prior to subcutaneous tunneling. The distal end of the catheter tube is selectively attachable to the hub assembly. Accordingly, after the tips of the catheter have been accurately positioned in a patient, the other end of the catheter may be reverse tunneled under the skin of a patient. Before or after tip placement, an incision is made in the skin adjacent to the point where the protruding distal end of the catheter exits the skin. A subcutaneous tunnel is then formed having a first end at the incision and a second end exiting the skin at a point remote from the first end of the tunnel, generally as the caudal direction. A sheath dilator is inserted into the tunnel, which is partially dilated so as to accommodate a tissue in-growth stabilizing cuff. The distal end of the catheter tube is routed through the subcutaneous tunnel and the cuff seated therein, thereby stabilizing the distal portion of the catheter tube in the patient. A selectively attachable hub assembly is connected to the lumens at the distal tip of the catheter tube for subsequent connection of the catheter to a fluid exchange device, such as a dialysis machine.

While the selectively attachable hub assembly described above facilitates tunneling a multi-lumen catheter in a patient, the separable hub assembly creates the need to connect the hub to a distal end of a multi-lumen catheter tube, thereby adding an additional step to the catheter insertion/connection procedure, which increases surgical time and expense. Furthermore, the hub-catheter connection provides an additional connection which may leak or separate from the catheter tube due to external loads on the hub such as by pulling or snagging. In addition, the attachable hub assembly is a relatively complex part, which makes it difficult to manufacture and, therefore, use of the hub assembly increases the cost of the catheter itself.

Therefore, there is a need for multi-lumen catheter that can be inserted into a patient using a reverse tunneling technique, which permits accurate placement of the tips of the catheter into the area to be catheterized and that is selectively attachable to a fluid exchange device. The improved catheter should not require an extensive hub assembly, thus making it relatively inexpensive to manufacture and easy to insert into a patient.

SUMMARY OF THE INVENTION

A multi-lumen catheter is provided for use in hemodialysis and the like. The multi-lumen catheter includes an elongated, central, multi-lumen tube portion having a distal end and a proximal end. The central tube portion has a substantially cylindrical outer shape and is internally segmented into a plurality of lumens. A distal branch portion includes a plurality of single-lumen distal extension tubes. Each distension tube has a proximal first end and a distal second end. The proximal first end of each distal extension tube is connected to the distal end of the central tube portion such that the single lumen of each distal extension tube is in fluid communication with one of the plurality of lumens of the central tube portion. A proximal branch portion includes a plurality of single-lumen proximal extension tubes. Each proximal extension tube has a distal first end and a proximal second end. The distal first end of each proximal extension tube is connected to the proximal end of the central tube portion such that the single lumen of each distal extension tube is in fluid communication with one of the plurality of lumens of the central tube portion. A plurality of selectively attachable connector hubs are provided, each connector hub being configured to be selectively attachable to the distal second end of one of the distal extensions and being configured for selective connection to a fluid exchange device. Each lumen of the central tube portion and the lumens of the distal and proximal extension tubes in fluid communication therewith define a flow path through the catheter. An in-growth stabilizing cuff may be affixed to an outer portion of the central tube portion.

The multi-lumen catheter may include a central tube portion having two lumens. In such a catheter, the distal branch portion includes two distal extension tubes, and the proximal branch portion includes two proximal extension tubes. The catheter may be arranged such that the plurality of single-lumen distal extension tubes of the distal branch portion converge to form a distal multi-lumen connecting portion which connects to the distal end of the central tube portion, and the plurality of single-lumen proximal extension tubes comprising the proximal branch portion converge to form a proximal multi-lumen connecting portion which connects to the proximal end of the central tube portion.

The central tube portion, the distal extension tubes, and the proximal extension tubes may be comprised of a fusible material, and the distal extension tubes and proximal extension tubes may be respectively fused to the distal and proximal ends of the central tube portion. The distal extension tubes may have a substantially cylindrical outer shape near their distal second ends, and the proximal multi-lumen connecting portion may also have a substantially cylindrical outer shape. The proximal extension tubes may have a substantially D-shaped cross-section over at least a portion of their length. Also, the proximal extension tubes may be substantially parallel to each other in a free state, and the proximal second ends of the distal extension tubes may be longitudinally spaced from each other.

The multi-lumen catheter may further include a plurality of connector hubs for connecting the catheter to a fluid exchange device. Each connector hub may be configured to be connected to the distal second end of one of the distal extension tubes, and configured for connection to a portion of a fluid exchange device. Each of the proximal extension tubes may include a tube wall, and each of the proximal extension tubes may include at least one opening extending through its tube wall. Further, an external portion of at least one of the distal extension tubes may include indicia which indicates a discrete flow path through the catheter. In one arrangement, the two proximal extension tubes have longitudinal axes which intersect at an included angle in a free state, the included angle being in a range from about 10 degrees to about 30 degrees.

A y-shaped catheter junction for a multi-lumen catheter is also provided. The y-shaped junction includes a dual-lumen trunk, having a substantially cylindrical outer wall, a first end, a second end, a first lumen, and a second lumen. A first single-lumen extension tube is connected to the first end of the trunk, such that the single lumen of the first single-lumen extension tube is in fluid communication with the first lumen of the trunk. A second single-lumen extension tube is connected to the first end of the trunk such that the single lumen of the second single-lumen extension tube is in fluid communication with the second lumen of the trunk. The y-shaped junction is arranged such that the first lumen of the trunk and the first extension tube define a first flow path, and the second lumen of the trunk and the second extension tube define a second flow path. The y-shaped catheter junction may also be arranged such that the first and second extension tubes have longitudinal axes which intersect at an included angle near the first end of the trunk in a free state, the included angle being in a range from about 10 degrees to about 30 degrees.

A method of forming a multi-lumen catheter is also disclosed. The method includes attaching a first plurality of single-lumen extension tubes to a distal end of a length of multi-lumen tubing comprising a plurality of multiple lumens, and attaching a second plurality of single-lumen extension tubes to a distal end of the length of multi-lumen tubing. Each single lumen of each extension tube is in fluid communication with one of the lumens of the length of multi-lumen tubing. The length of multi-lumen tubing may include two lumens, and the first and second pluralities of extension tubes may form substantially y-shaped junctions on each end of the length of multi-lumen tubing.

The method of forming a multi-lumen catheter may include first forming a y-shaped distal junction. The process may include providing a first length of single-lumen tubing to form a distal arterial extension tube, providing a second length of single-lumen tubing to form a distal veinal extension tube, providing a first length of multi-lumen tubing comprising at least an arterial lumen and a veinal lumen, and having a distal end and a proximal end, attaching an end of the distal arterial extension tube to the distal end of the first length of multi-lumen tubing such that the distal arterial extension tube is in fluid communication with the arterial lumen of the first length of multi-lumen tubing, and attaching an end of the distal veinal extension tube to the distal end of the first length of multi-lumen tubing such that the distal veinal extension tube is in fluid communication with the veinal lumen of the first length of multi-lumen tubing. The proximal end of the first length of multi-lumen tubing forms a connecting end.

A second length of multi-lumen tubing having a distal end and a proximal end is provided. The tubing includes an arterial lumen and a veinal lumen. The connecting end of the first length of multi-lumen tubing is connected to the distal end of the second length of multi-lumen tubing, such that the arterial extension tube of the distal junction is in fluid communication with the arterial lumen of the second length of multi-lumen tubing, and the veinal extension tube of the distal junction is in fluid communication with the veinal lumen of the second length of multi-lumen tubing.

A y-shaped proximal junction is also formed. This process includes providing a third length of single-lumen tubing to form a proximal arterial extension tube, and providing a fourth length of single-lumen tubing to form a proximal veinal extension tube. A third length of multi-lumen tubing is also provided which includes at least an arterial lumen and a veinal lumen, and has a distal end and a proximal end. An end of the proximal arterial extension tube is attached to the distal end of the third length of multi-lumen tubing such that the proximal arterial extension tube is in fluid communication with the arterial lumen of the third length of multi-lumen tubing. Also, an end of the proximal veinal extension tube is attached to the distal end of the third length of multi-lumen tubing such that the proximal veinal extension tube is in fluid communication with the veinal lumen of the third length of multi-lumen tubing. The distal end of the third length of multi-lumen tubing forms an attachment end.

The attachment end of the third length of multi-lumen tubing is attached to the proximal end of the second length of multi-lumen tubing, such that the arterial extension tube of the proximal junction is in fluid communication with the arterial lumen of the second length of multi-lumen tubing, and the veinal extension tube of the proximal junction is in fluid communication with the veinal lumen of the second length of multi-lumen tubing. The method may also include forming at least one opening in a wall of the proximal veinal extension tube, and forming at least one opening in a wall of the arterial proximal extension tube. The steps of attaching extension tubes and lengths of multi-lumen tubing together or to each other may include heat welding or similar fusing techniques. The longitudinal axes of the distal arterial extension tube and distal veinal extension may be arranged to intersect at an included angle in a free state in a range from about 10 degrees to about 30 degrees.

A method for surgically implanting a double-Y-shaped multi-lumen catheter into a patient is also provided. The method is suited for implanting a multi-lumen catheter having an elongated, central, multi-lumen tube portion, a proximal end portion including a single-lumen proximal veinal extension tube and a single-lumen proximal arterial extension tube each having a proximal tip, and a distal end portion including a single-lumen distal veinal extension tube and a single-lumen distal arterial extension tube each having a distal end. The method includes making an incision in the skin of the patient, and inserting the proximal tips of the proximal veinal and arterial extension tubes through the incision and placing the proximal tips in the patient. A subcutaneous tunnel is formed having a first end proximate to the incision and a second end remote from the first end of the tunnel. The distal veinal and arterial extension tubes and at least a portion of the central tube portion are guided through the subcutaneous tunnel such that at least the distal ends of the distal veinal and arterial extension tubes extend outwardly from the tunnel through the second end of the tunnel. At least a portion of the distal end portion of the catheter is secured to the patient such as by sutures or any other suitable means.

When the catheter includes a stabilizing cuff, the method may further include dilating at least a portion of the subcutaneous tunnel to receive the cuff. Dilation of the tunnel may be accomplished by sliding a sheath dilator along the shaft of a trocar longitudinally positioned within the tunnel. The distal end portion of the catheter is secured to the patient by seating the cuff in a dilated portion of the subcutaneous tunnel.

The catheter implanting method may further include respectively connecting the distal arterial and veinal extension tubes to arterial and veinal legs of a fluid exchange device. Connecting the distal arterial and veinal extension tubes may include connecting the distal arterial extension tube to the arterial leg with a first connector hub, and connecting the proximal veinal extension tubes to the veinal leg with a second connector hub. Inserting the proximal tips of the proximal veinal and arterial extension tubes into a patient may include placing the proximal tip of the veinal extension tube into a vein in the patient, and placing the proximal tip of the arterial extension tube into an artery in the patient.

These and other aspects of the invention will be made clear from a reading the following detailed description together with the drawings.

DETAILED DESCRIPTION

For the purposes of the following description and the claims appended hereto, the relative term "proximal" refers to those portions of a catheter and those portions of components of the catheter which are nearest the insertion end of the catheter, that is, the end of the catheter that is inserted into an area of a patient's body being catheterized, such as a blood vessel. Conversely, the relative term "distal" refers to those portions of a catheter and those portions of components of the catheter which are farthest from the insertion end of the catheter.

Figure 1:
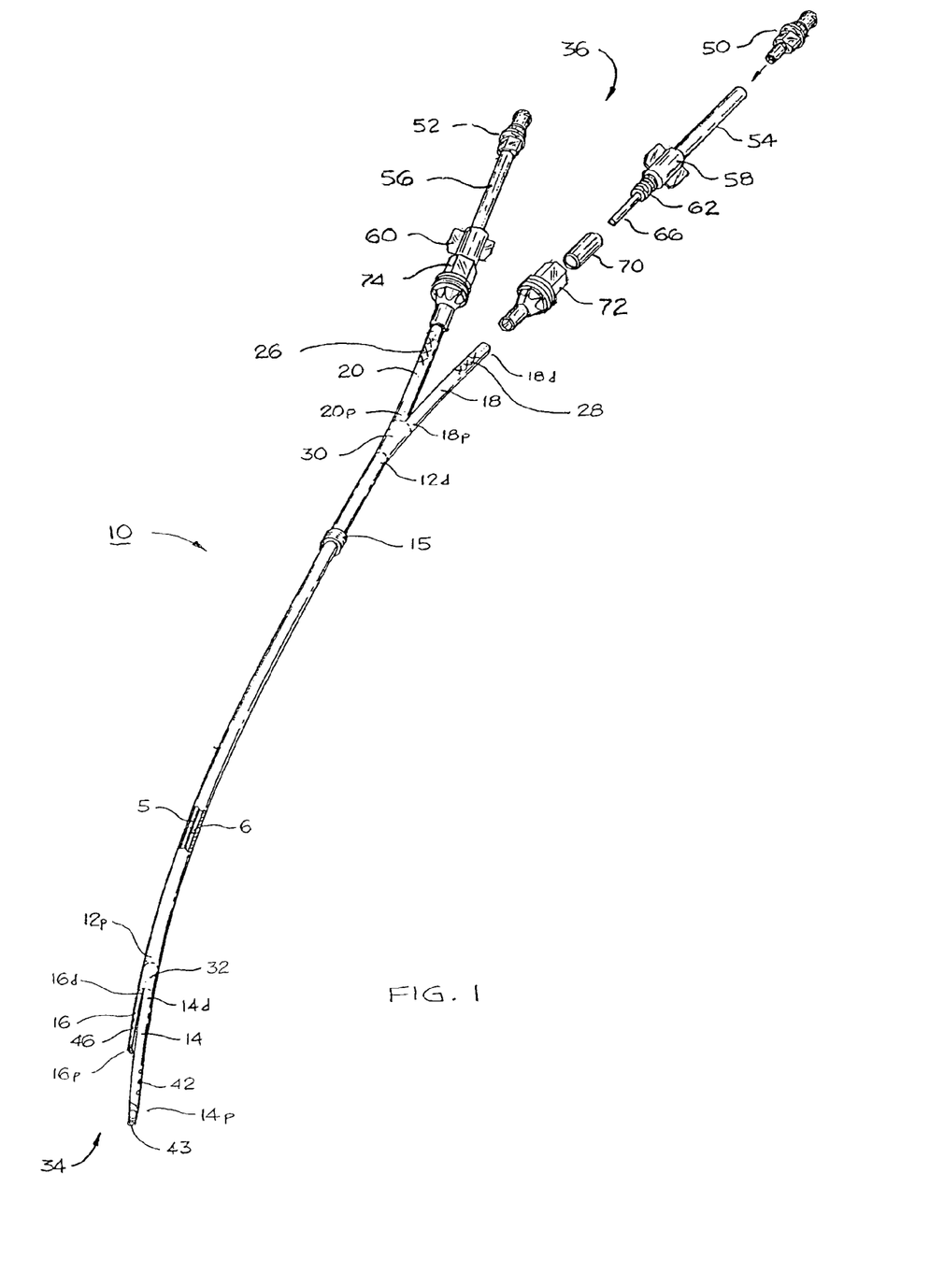
FIG. 1 is a perspective view of a double y-shaped multi-lumen catheter.

FIG. 1 shows a double-Y-shaped multi-lumen catheter 10 according to the present invention. The catheter 10 includes a proximal end 34 for insertion into a patient, and a distal end 36 for connection to a fluid exchange device, such as a dialysis machine or the like. The catheter 10 includes an elongated, central, multi-lumen tube portion 12, a plurality of proximal single-lumen extension tubes 14, 16, and a plurality of distal single-lumen extension tubes 18, 20. In the embodiment shown, the central tube portion 12 includes an arterial lumen 5 and a veinal lumen 6. In this arrangement, the catheter 10 includes a proximal veinal extension tube 14 and a distal veinal extension tube 18 in fluid communication with the venal lumen 6, and a proximal arterial extension tube 16 and a distal arterial extension tube in fluid communication with the arterial lumen 5. The catheter 10 may include a stabilizing cuff 15 affixed to an outer portion of the central tube portion 12 as shown in FIG. 1. Preferably, the cuff 15 is longitudinally positioned on the central tube portion 12 such that the cuff 15 will be finally positioned in a subcutaneous tunnel in a patient as described more fully below.

Figure 2:
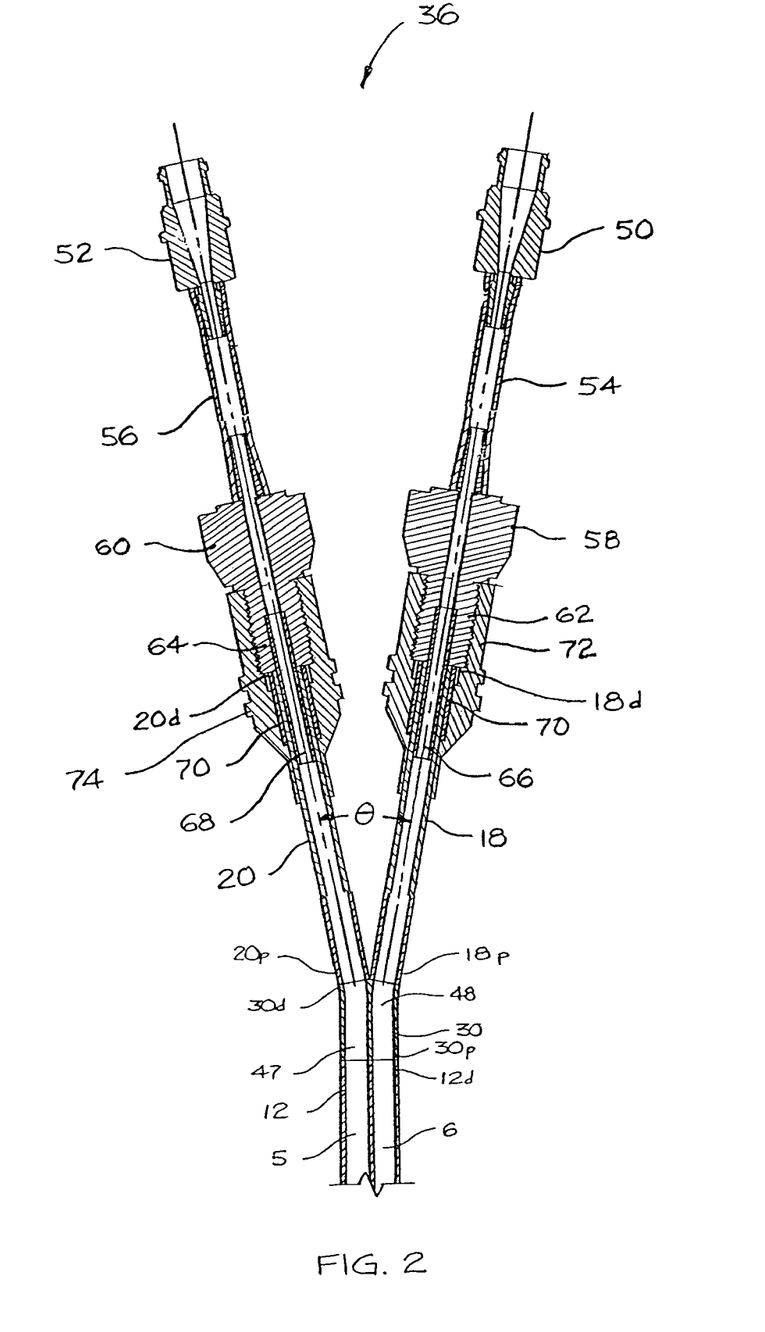
FIG. 2 is a cross-sectional view of a distal portion of the multi-lumen catheter of FIG. 1.
Figure 3:
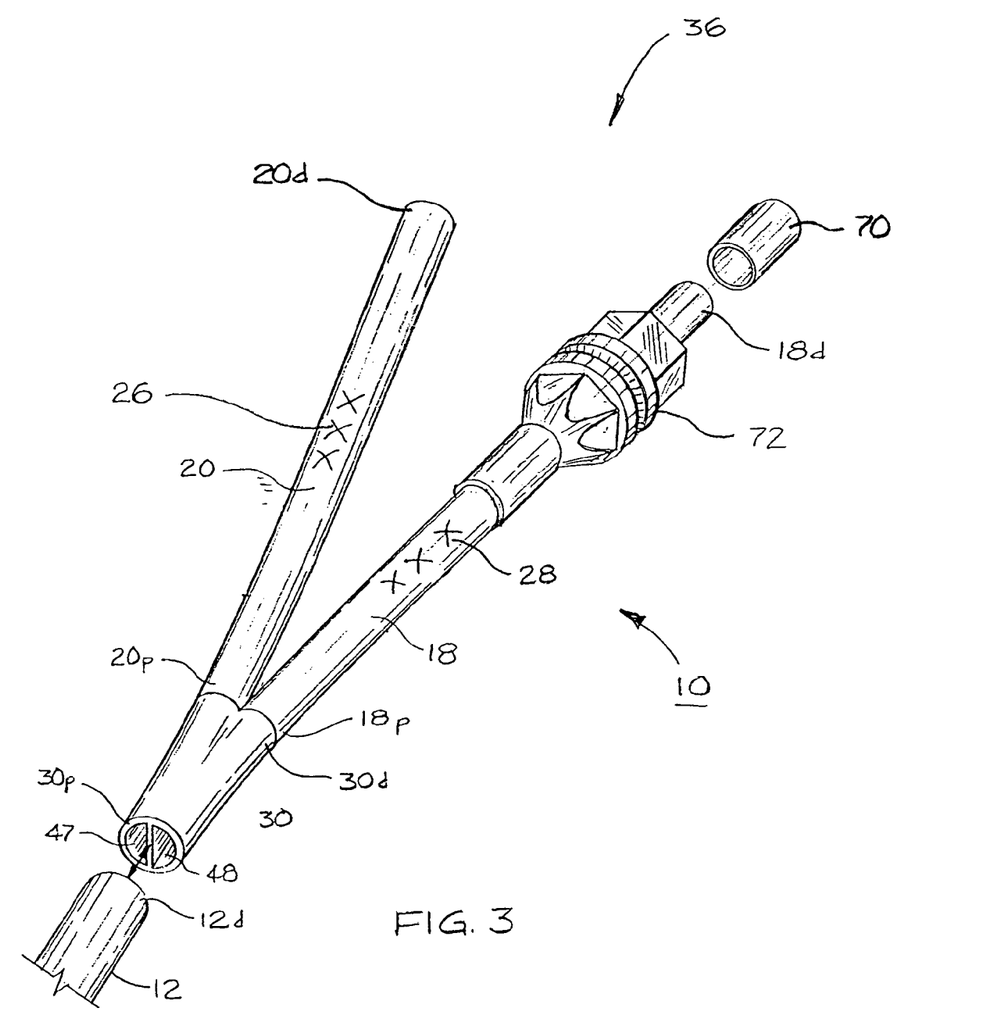
FIG. 3 is a partially exploded detail perspective view of a distal portion of the multi-lumen catheter of FIG. 1.

A construction for the distal end 36 of the multi-lumen catheter 10 is shown in FIGS. 1-3. As shown in FIGS. 2 and 3, the proximal ends 18p, 20p of the distal extension tubes 18, 20 may be connected to a distal end 12d of the central tube portion 12 by a distal multi-lumen trunk 30. The multiple lumens of the distal trunk 30 correspond in number to the multiple lumens of the central tube portion 12 and the number of distal extension tubes 18, 20. In the illustrated embodiment, the distal trunk 30 includes a veinal distal trunk lumen 48, and an arterial distal trunk lumen 47 as shown in FIG. 2.

As shown in FIG. 3, the proximal ends 18p, 20p of the distal extension tubes 18, 20 are connected to the distal end 30d of the distal trunk, thereby forming a substantially Y-shaped junction. The proximal end 30p of the distal trunk 30 is connected to the distal end 12d of the central tube portion 12 as shown in FIG. 2, thereby forming a Y-shaped distal end 36. Preferably, the proximal end 30p of the distal trunk 30 is substantially cylindrical in shape, and is substantially equal in outer diameter to the outer diameter of the central tube portion 12, thereby providing a smooth transition at the juncture between the distal trunk 30 and the central tube portion 12.

As shown in FIG. 2, the distal extension tubes are arranged such that an included angle "?" exists between the longitudinal axes of the tubes 18, 20 in a free state. In a preferred arrangement, the angle "?" ranges from about 10 degrees to about 30 degrees. The distal extension tubes 18, 20 can be arranged, however, so that the angle "?" is any desired angle. The veinal distal trunk lumen 48 is in fluid communication with the veinal lumen 6 of the central tube portion 12 and the single lumen of the distal extension tube 18. Similarly, the arterial distal trunk lumen 47 is in fluid communication with the arterial lumen 5 of the central tube portion 12 and the single lumen of the distal arterial extension tube 20.

In an alternative arrangement, the distal extension tubes 18, 20 may be connected directly to the distal end 12d of the central tube portion 12 rather than to an interconnected distal trunk 30 (not shown). In either arrangement, the mating end portions of the distal extension tubes 18, 20, the distal end of the central tube portion 12d, and/or the distal trunk 30 are sealably fused together by heat welding or the like such that the fluid communication between the interconnecting lumens of the components is established and maintained and no leakage occurs at the connections.

As shown in FIGS. 1-3, the catheter 10 also includes selectively attachable connector hubs 72, 74 on the distal ends 18d, 20d of the distal extension tubes 18, 20. As will be described in detail below, the connector hubs 72, 74 are selectively attachable so that the connector hubs 72, 74 can be attached to and removed from the distal end 36 of the catheter 10 after insertion of the proximal end 34 of the catheter 10 into a patient, and after reverse, subcutaneous tunneling of the distal end 36 As shown in FIGS. 1 and 2, the connector hubs 72, 74 are configured for selective sealable attachment between the distal ends 18d, 20d of the distal extension tubes 18, 20 and legs of a fluid exchange device. The connector hubs. The veinal connector hub 72 is selectively attachable to the distal portion 18d of the distal veinal extension tube 18, and the arterial connector hub 74 is selectively attachable to the distal portion 20d, of the distal arterial extension tube 20.

In one embodiment as shown in FIGS. 1-3, the selectively attachable hubs 72, 74 are connectable with mating compression fittings 58, 60. The compression fittings may include cannulae 66, 68 and threaded male portions 62, 64 that matingly engage the distal extension tubes 18, 20 and the connector hubs 72, 74 as shown in FIG. 2. When fully engaged, the hubs 72, 74 and compression fittings 58, 60 compress compression sleeves 70 about the distal portions 18d, 20d of the distal extension tubes 18, 20, thereby forming sealed connections. The compression fittings 58, 60 may be further connected to luer-type fittings 50, 52 or the like by connector tubes 54, 56. The luer-type fittings 50, 52 may then be connected to corresponding luer-type connection mechanisms on a fluid exchange device 200. For example, the distal ends of the luer-type fittings 50, 52 may include quarter-turn type threads for leak-tight engagement with matching quarter-turn fittings on the veinal and arterial legs of a fluid exchange device 200. Other types of know leak-tight selectively attachable connection configurations may also be used.

As shown in FIGS. 1 and 3, the connector hubs 72, 74 can be selectively attached to the distal ends 18d, 20d of the distal extension tubes 18, 20. This arrangement permits the distal end 36 of the catheter 10 to be subcutaneously reverse tunneled in a patient as described more fully below without interference from the hubs 72, 74. After the distal end of the catheter 10 is subcutaneously reverse tunneled in a patient such that the distal end 36 protrudes outwardly from the patient, the hubs 72, 74 can be backfit over the distal ends of distal extension tubes 18, 20 as shown for hub 72 in FIG. 3. The compression sleeves 70 can then be placed over the distal ends 18d, 20d of the extension tubes 18, 20, and the sealed connections can be completed as shown in FIG. 2. The catheter 10 can then be connected to a fluid exchange device 200.

Figure 4:
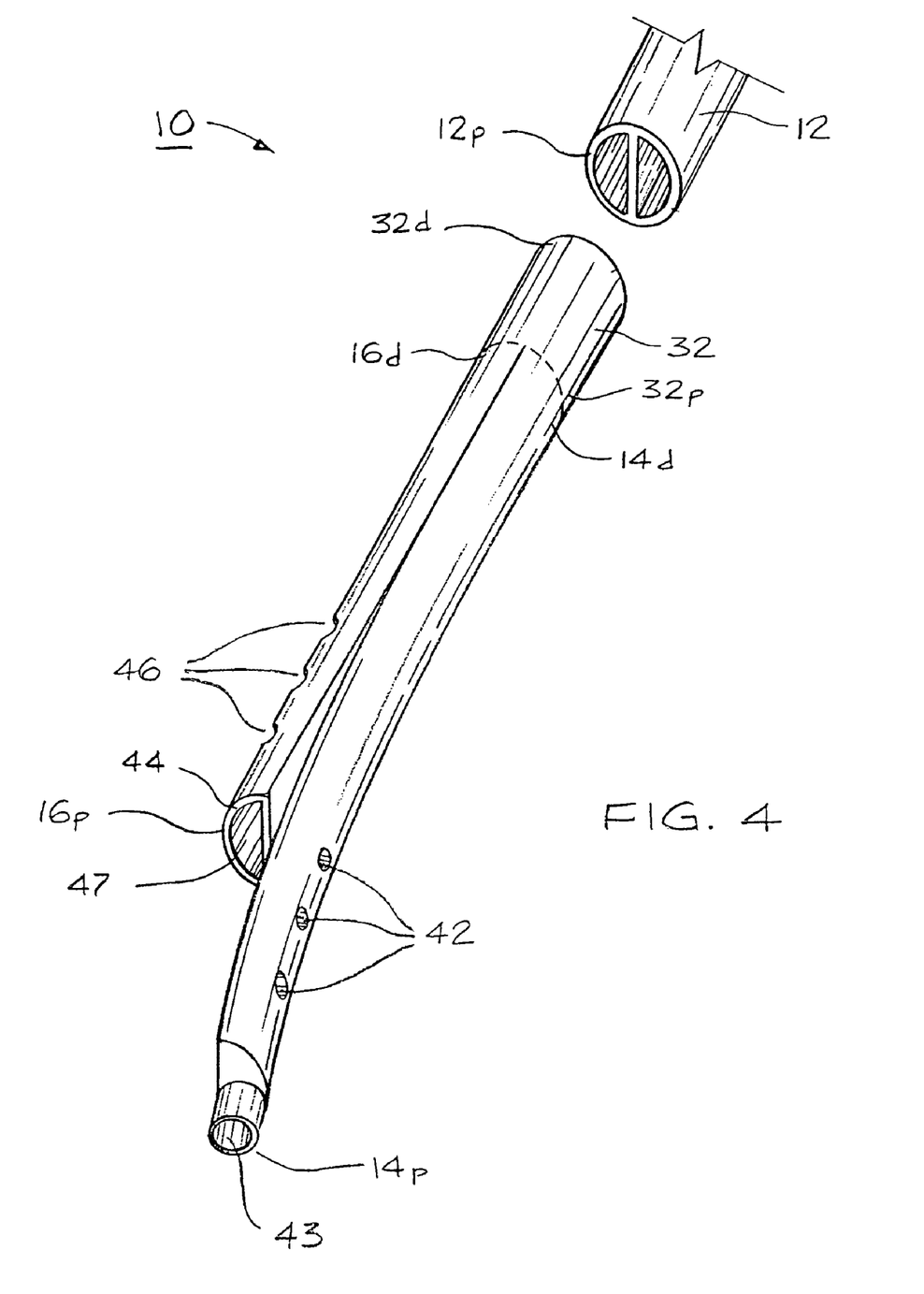
FIG. 4 is a partially exploded detail perspective view of a proximal portion of the multi-lumen catheter of FIG. 1.
Figure 5:
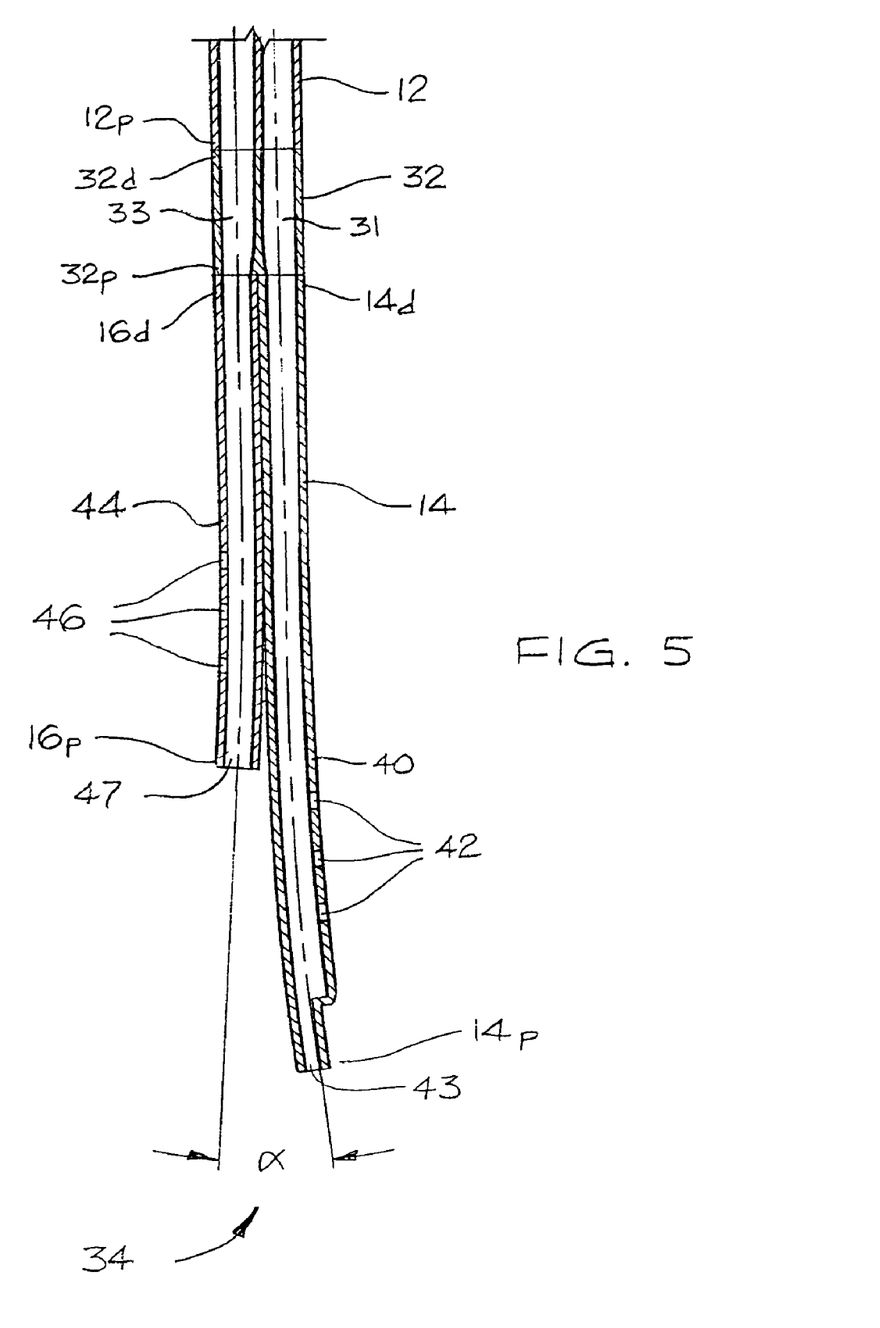
FIG. 5 is a cross-sectional view of a proximal portion of the multi-lumen catheter of FIG. 1.

A construction for the proximal end 34 of the catheter 10 is shown in FIGS. 1, 4, and 5. The distal ends 14d, 16d of the proximal extension tubes 14, 16 may be connected to a proximal end 12p of the central tube portion 12 by a proximal multi-lumen trunk 32. The lumens of the proximal trunk 32 correspond in number to the multiple lumens of the central tube portion 12 and to the number of proximal extension tubes 14, 16. In the illustrated embodiment, the proximal trunk 32 includes a vienal proximal trunk lumen 31, and an arterial proximal trunk lumen 33 as shown in FIG. 5. As shown in FIG. 4, the distal ends 14d, 16d of the proximal extension tubes 14, 16 are connected to the proximal end 32p of the proximal trunk 32, thereby forming a substantially Y-shaped junction. The distal end 32d of the proximal trunk 32 is connected to the proximal end 12p of the central tube portion 12 as shown in FIG. 5, thereby forming a substantially Y-shaped proximal end 34 on the catheter 10. Preferably, the distal end 32d of the proximal trunk 32 is substantially cylindrical in shape, and is substantially equal in outer diameter to the outer diameter of the central tube portion 12, thereby providing a smooth transition at the juncture between the proximal trunk 32 and the central tube portion 12.

As shown in FIG. 5, the proximal extension tubes are arranged such that an included angle "a" exists between the longitudinal axes of the tubes 14, 16 in a free state. In a preferred arrangement, the angle "a" is about 5 degrees in a rest position or free state. The proximal extension tubes 14, 16 can be arranged, however, so that the angle "a" is any desired angle. The veinal proximal trunk lumen 31 is in fluid communication with the veinal lumen 6 of the central tube portion 12 and the single lumen of the proximal veinal extension tube 14. Similarly, the arterial proximal trunk lumen 33 is in fluid communication with the arterial lumen 5 of the central tube portion 12 and the single lumen of the proximal arterial extension tube 16.

In an alternative arrangement, the proximal extension tubes 14, 16 may be connected directly to the proximal end 12p of the central tube portion 12 rather than to an interconnecting proximal trunk 32 (not shown). In either arrangement, the mating end portions of the proximal extension tubes 14, 16, the proximal end of the central tube portion 12p, and/or the proximal trunk 32 are sealably fused together, such as by heat welding or the like, such that the fluid communication between the interconnected lumens of the components is established and maintained and no leakage occurs at the connections.

As shown in FIGS. 1, 4, and 5, the proximal arterial extension tube 16 is preferably shorter in length than the proximal veinal extension tube 14. For example, the proximal arterial extension tube 16 may be about 4 cm shorter in length than the proximal veinal extension tube 14. The resulting longitudinal spacing between the proximal tips 14p and 16p facilitates optimal proximal tip placement in a patient. As shown in FIG. 4, the proximal veinal extension tube 14 may include an end opening 43 in or near its proximal tip 14p. The proximal veinal extension tube 14 may also include one or more transverse openings 42 in its tube wall 40. Similarly, as also shown in FIG. 4, the proximal arterial extension tube 16 may include an end opening 47 in or near its proximal tip 16p. The proximal arterial extension tube 16 may also include one or more transverse openings 46 in its tube wall 44. The openings 42, 43, 46, and 47 facilitate fluid flow into or out from the proximal extension tubes 14, 16.

Figure 6A:
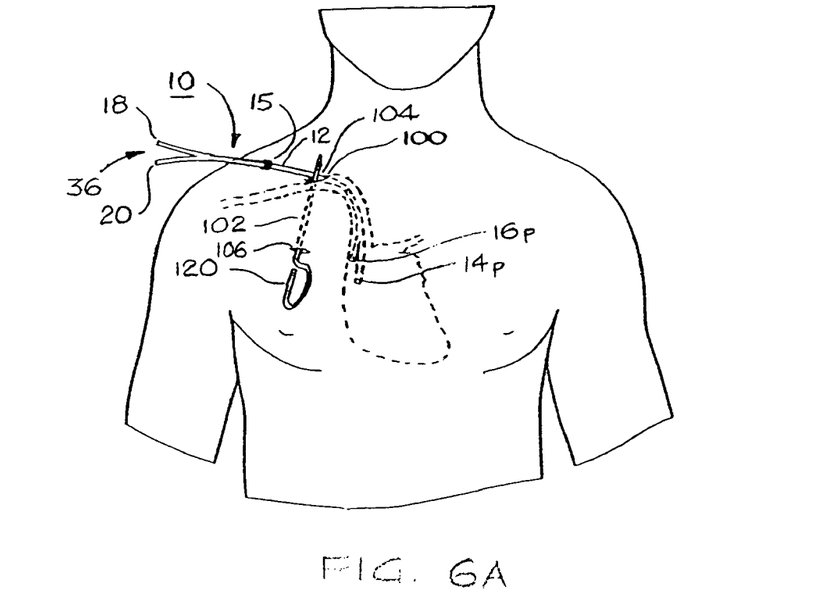
FIGS. 6A-6D illustrate a procedure for tunneling a multi-lumen catheter like that of FIG. 1 in a patient.

The hubs 72 and 74 are selectively attachable and detachable from the distal end 36 of the catheter 10 to facilitate tunneling the catheter 10 in a patient. A method of installing a catheter 10 in a patient is illustrated in FIGS. 6A-6D. As shown in FIG. 6A, an incision 100 is made in the skin of a patient. The proximal tips 14p, 16p of catheter 10 are inserted through the incision 100 and are placed at desired locations within the patient using conventional techniques, such as the Seldinger technique.

At this stage, the distal end 36 and distal portions of the catheter 10 extend outwardly from the incision 100. A trocar 120 or other suitable instrument is used to form a subcutaneous tunnel 102 having a first end 104, which is preferably coincident with the incision 100, and an opposed second end 106, which is remote from the first end 104, as shown in FIG. 6A.

Figure 6B:
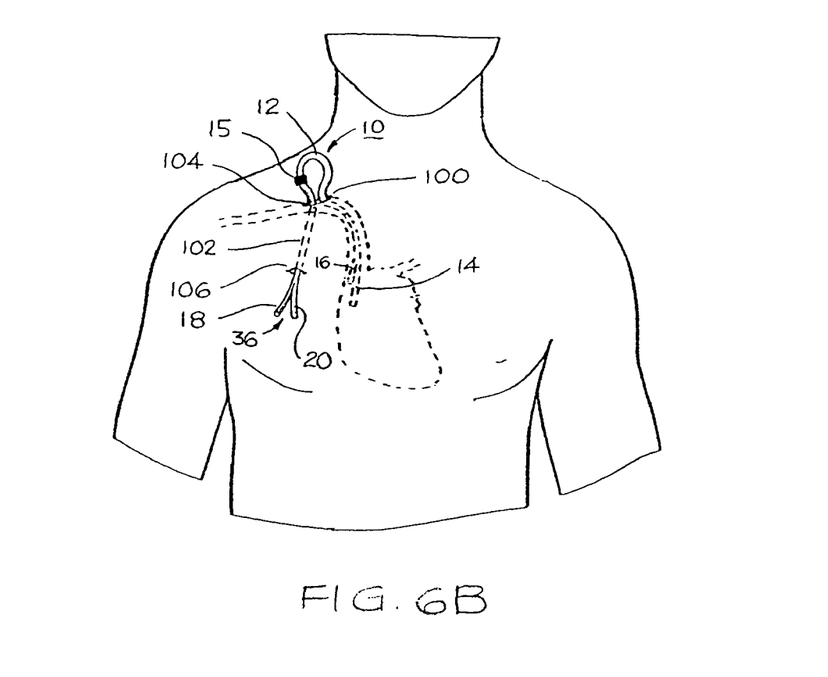

As shown in FIG. 6B, the distal end 36 of the catheter 10 is inserted through the first end 104 of the tunnel 102, and the distal end 36 is guided through the tunnel 102 such that the distal end 36 extends out from the tunnel 102 at its second end 106. The distal extension tubes 18, 20 are sufficiently flexible that they may be bundled or clamped together by any suitable means to facilitate passing the Y-shaped distal end 36 of the catheter 10 through the tunnel 102.

Figure 8A:
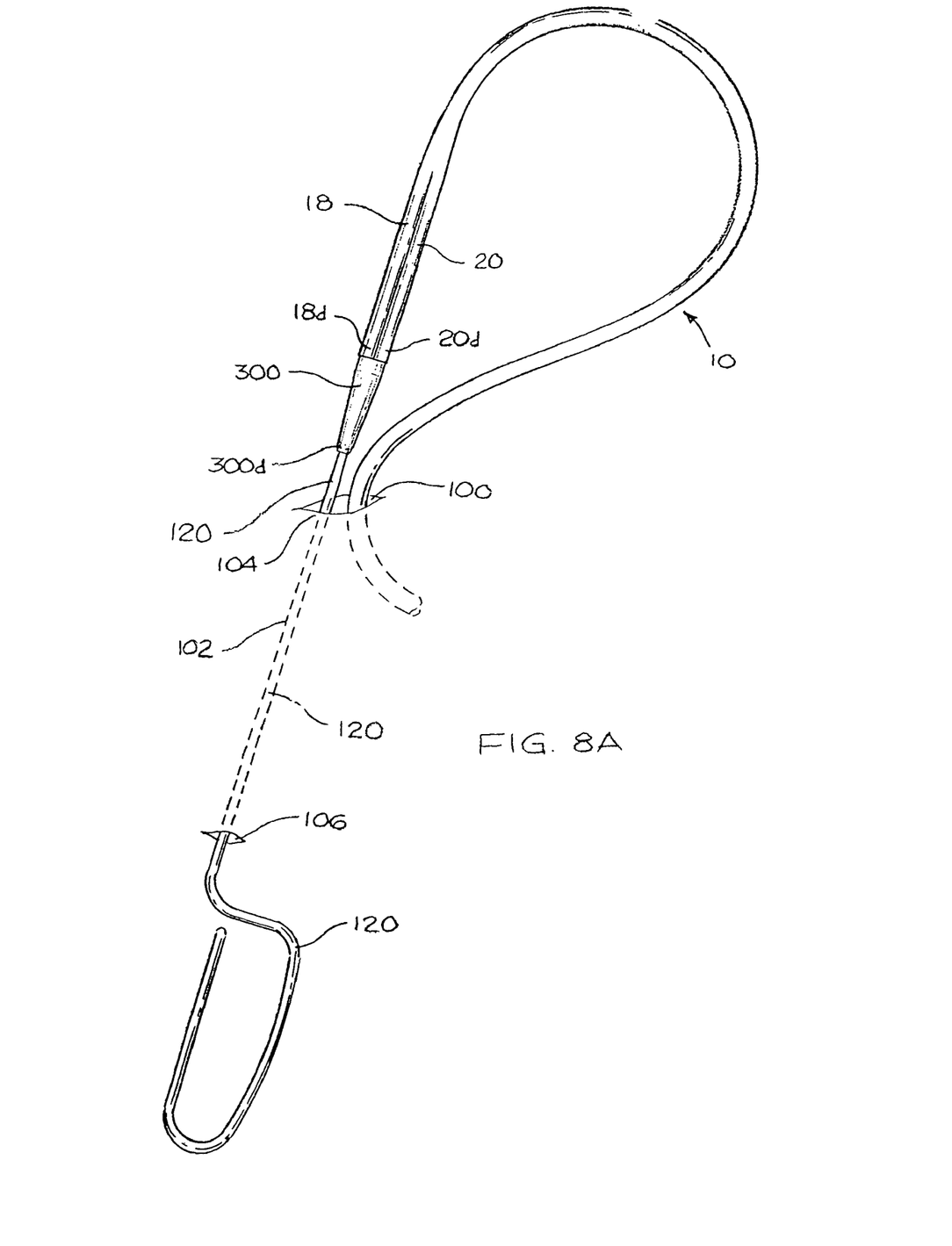
FIGS. 8A-8C are views of a connection between a distal end of the catheter and a trocar for guiding the catheter through a subcutaneous tunnel.
Figures 8B, 8C:
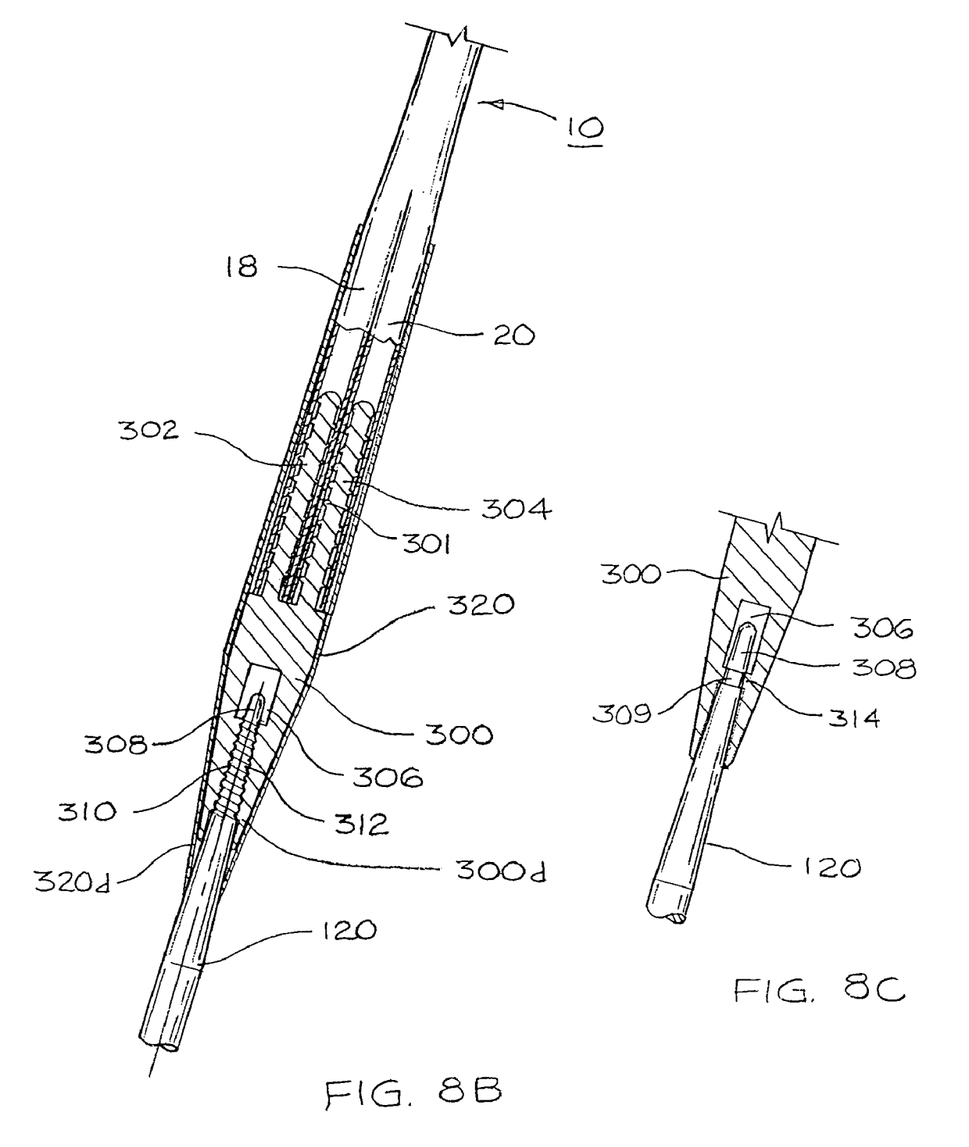

In a preferred arrangement as shown in FIGS. 8A and 8B, the distal ends 18d, 20d of the distal extension tubes 18, 20 are attached to a connector 300. The proximal end of the connector 300 may include a first tip 302 and a second tip 304 as shown. The tips 302, 304 are insertable into the lumens at the distal ends 18d, 20d of the distal extension tubes 18, 20. The tips 302, 304 preferably include ribs 301 or the like to tightly engage within the distal ends 18d, 20d of the distal extension tubes 18, 20 such that the connector 300 is securely but removably attached to the extension tubes 18, 20. When the tips 302, 304 are respectively engaged in the distal extension tubes 18, 20, the connector 300 holds the distal extension tubes 18, 20 in close arrangement as shown so that the distal extension tubes 18, 20 can be simultaneously subcutaneously tunneled in a patient as described below. The distal end of the connector 300d preferably includes a bore 306 which is configured to attachably receive an insertion tip 308 of the trocar 120. The bore 306 may include threads 310 which can be engaged with mating threads 312 on the insertion tip 308 of the trocar 120. Alternatively, the bore 306 may include a collar portion 314 which snaps into a groove 309 on the insertion tip 308 of the trocar 120 as shown in FIG. 8C. In this way, the distal end 300d of the connector 300 can be engaged on the insertion tip 308 of the trocar 120 to route the attached distal extension tubes 18, 20 through the subcutaneous tunnel 102 with the trocar 120. Once the distal end 36 of the catheter 10 has been drawn through the tunnel 102, the connector 300 can be disengaged from the distal extension tubes 18, 20.

In order to provide the distal portions of the catheter 10 with a smooth and compact outer profile to facilitate passage of the distal end 36 of the catheter 10 through the tunnel 102, a sheath 320 may be used as shown in FIG. 8B. The sheath 320 is placed over at least a portion of the connector 300 and the distal extension tubes 18, 20. Preferably, the distal end 320d of the sheath 320 is tapered as shown. The sheath 320 and the distal portions of the catheter 10 can be drawn together through the tunnel 102 with the trocar 120. The sheath 320 is removed from the catheter 10 once the distal portions of the catheter 10 have been drawn through the tunnel 102.

Figure 6C:
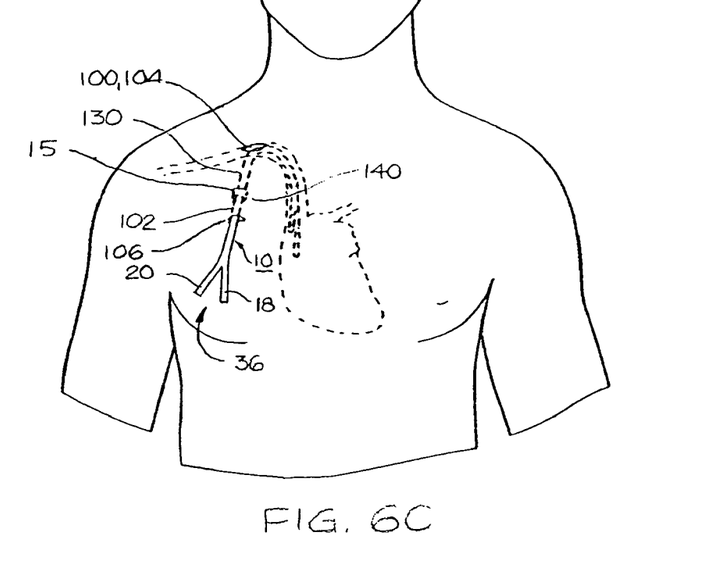

As shown in FIG. 6C, the distal end 36 of the catheter 10 is drawn from the second end 106 of the tunnel 102 such that the distal extension tubes 18, 20 and at least a portion of the central tube portion 12 extends from the second end 106 and the catheter 10 is fully tunneled in the patient. The incision 100 and the second end 106 of the tunnel are suitably treated and dressed.

Figure 7:
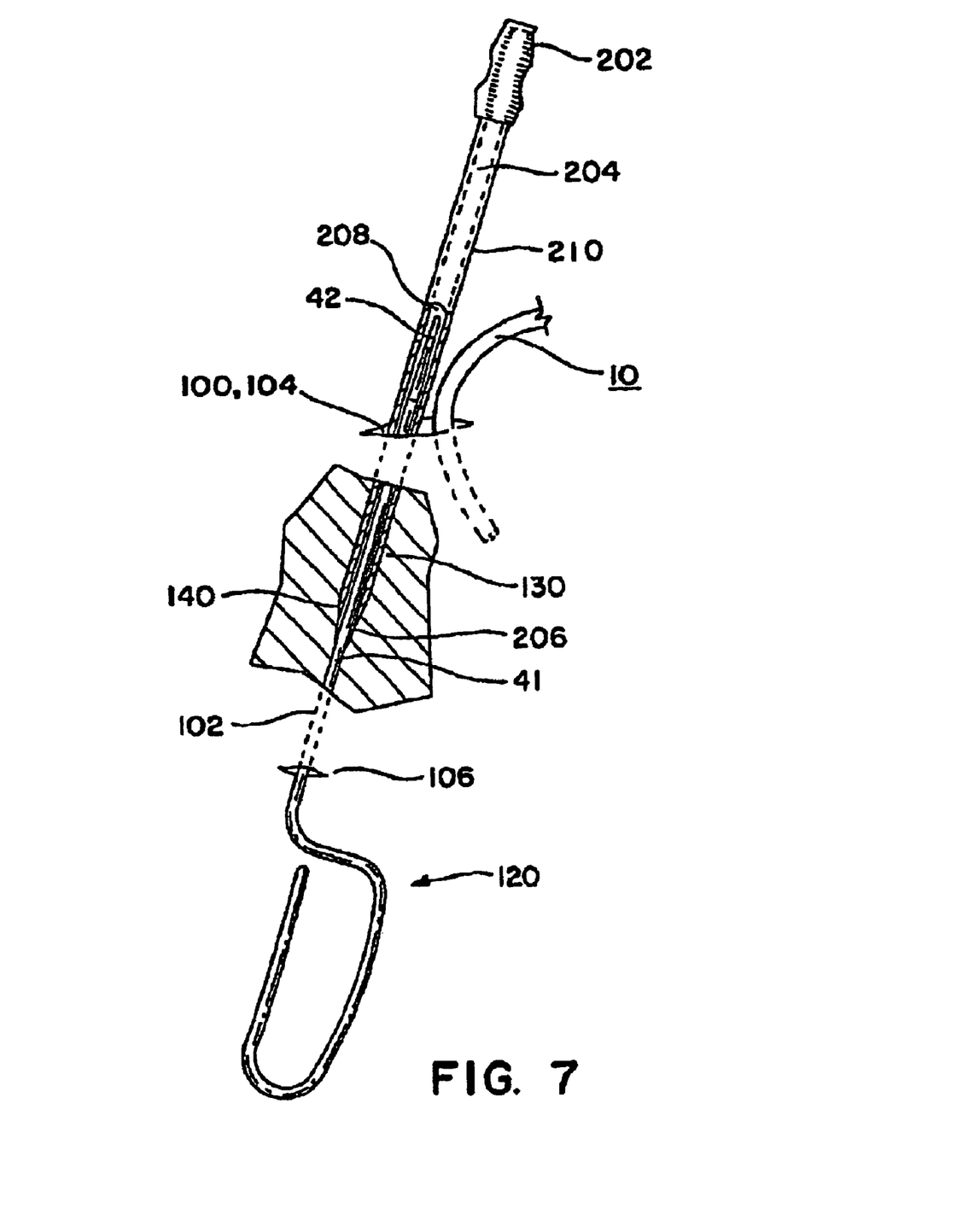
FIG. 7 is a partial sectional view of a sheath dilator engaged along a trocar to dilate a portion of a subcutaneous tunnel in a patient.

An outer portion of the central tube portion 12 may include a tissue in-growth stabilizing cuff 15, as shown in FIG. 1, for stabilizing the inserted catheter 10 in the patient. Referring to FIGS. 6C and 7, when the catheter 10 includes a stabilizing cuff 15, a portion 130 of tunnel 102 may be dilated to enlarge the width of the tunnel 102 to receive the cuff 15 as the catheter 10 is drawn through the tunnel 102. As shown in FIG. 7, the dilated portion 130 of the tunnel is preferably dilated by sliding a sheath dilator 210 over an end 42 and shaft 41 of the trocar 120 when the trocar 120 is positioned in the subcutaneous tunnel 102 as shown in FIG. 6A. The sheath dilator 210 preferably includes a hollow bore 208, a tapered leading end 206, a substantially cylindrical portion 204, and a handle 202. The sheath dilator 210 is inserted through the first end 104 of the tunnel 102 and into the tunnel 102 until the tip 206 has been inserted proximate to a cuff seating point 140 in the tunnel 102 to form a dilated portion 130 of the tunnel 102. Once the dilated portion 130 is sufficiently dilated, the sheath dilator 210 is removed from the tunnel 102 and the trocar 120. The catheter 10 is finally positioned in the tunnel 102 when the cuff 15 is seated near an end 140 of the dilated portion 130 of the tunnel 102 as shown in FIG. 6C.

Figure 6D:
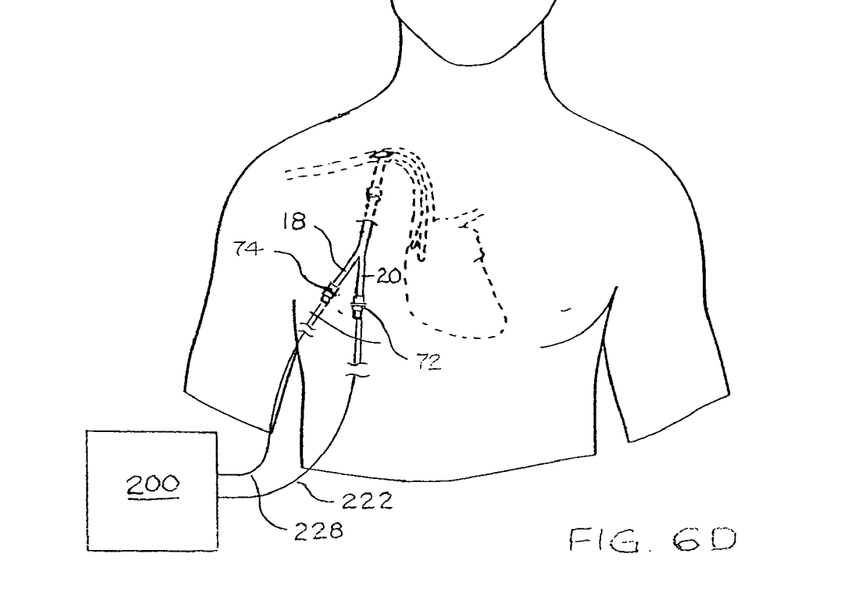

As shown in FIG. 6D, the catheter 10 is connected to a fluid exchange device 200. The distal end 18d of the distal venal extension tube 18 is selectively attached to a veinal leg 228 of the fluid exchange device 200 by connector hub 74. Similarly, the distal end 20d of the distal arterial extension tube 20 is selectively attached to an arterial leg 222 of the fluid exchange device 200 by connector hub 72. As shown in FIG. 3, indicia 26 and 28 may be included on the distal extension tubes 18, 20 and/or the connector hubs 72, 74 to assist medical personnel in identifying the proper distal extension tube 18 or 20 for connection to a corresponding leg of the fluid exchange device 200. The indicia 26, 28 may be markings, colors, or any other distinctive indicator.

While this invention has been illustrated and described in accordance with a preferred embodiment, it is recognized that variations and changes may be made therein without departing from the invention as set forth in the claims. Certain modifications and improvements will occur to those skilled in the art upon a reading of the forgoing description. For example, while the multi-lumen catheter has been described with reference to a catheter with two lumens, the invention also includes multi-lumen catheters including three or more lumens as required. It should be understood that all such modifications are not contained herein for the sake of conciseness and readability, but are properly within the scope of the following claims.

What is claimed is:

1. A method for surgically implanting a multi-lumen catheter into a patient, the multi-lumen catheter comprising a one-piece multi-lumen tube portion having a plurality of integrally formed lumens, a proximal end portion including a single-lumen proximal venous portion and a single-lumen proximal arterial portion, and a distal end portion including a single-lumen distal venous tube portion and a single-lumen distal arterial tube portion each having a distal end, the method comprising:
   (a) making an incision in the skin of the patient
   (b) inserting the proximal end of the catheter through the incision, into the patient;
   (c) forming a subcutaneous tunnel by a trocar or other suitable instrument; wherein the subcutaneous tunnel having a first end coincident to the incision and a second end, which is located a distance from the first end of the tunnel;
   (d) after the subcutaneous tunnel is completely formed, guiding the distal end of the catheter and at least a portion of the multi-lumen tube portion through the subcutaneous tunnel such that at least the distal ends of the distal venous and distal arterial tube portions extend outwardly from the second end of the tunnel.

2. A method according to claim 1, the method further comprising respectively connecting the distal arterial and distal venous tube portions of the catheter to an arterial leg and a venous leg of a fluid exchange device.

3. A method according to claim 2, wherein connecting the distal arterial and distal venous portions of the catheter to the arterial and venous legs of the fluid exchange device comprises connecting the distal arterial portion of the catheter to the arterial leg utilizing a first connector hub, and connecting the proximal venous portion of the catheter to the venous leg utilizing a second connector hub.

4. The method of claim 1, wherein inserting the proximal end of the catheter into the patient comprises:
   placing the proximal venous portion of the catheter into the circulatory system of the patient; and
   placing the proximal arterial portion of the catheter into the circulatory system of the patient.

5. The method of claim 1 wherein the multi-lumen catheter further comprises a stabilizing cuff affixed to an outer surface of the catheter, the step of guiding the distal end of the catheter and at least a portion of the multi-lumen tube portion through the subcutaneous tunnel further comprising placing the stabilizing cuff between the outer surface of the catheter and an interior wall of the subcutaneous tunnel.

6. The method of claim 5 further comprising dilating at least a portion of the subcutaneous tunnel before guiding the distal end of the catheter and at least a portion of the multi-lumen tube portion through the subcutaneous tunnel, wherein the dilating step comprises sliding a sheath dilator along a shaft of a trocar longitudinally positioned in the tunnel.

7. The method of claim 6 further comprising seating the stabilizing cuff in a dilated portion of the subcutaneous tunnel.

8. The method of claim 1 wherein the step of guiding the distal end of the catheter and at least a portion of the multi-lumen tube portion through the subcutaneous tunnel further comprises the steps of:
   (a) attaching an attachment end of a trocar to the distal end of the catheter; and
   (b) passing the attachment end of the trocar, with the distal end of the catheter attached, through the subcutaneous tunnel.

9. The method of claim 8 further comprising placing a sheath having a smooth outer contour over the attachment end of the trocar where it attaches to the distal end of the multi-lumen catheter.

10. A method for placing a catheter into the vasculature of a patient, the catheter comprising a central one-piece multi-lumen portion having a plurality of integrally formed lumens, a proximal end portion and a distal end portion, each of the proximal and distal end portions comprising single-lumen catheters not connected to each other along a substantial portion thereof, the method comprising:
   (a) making an incision in the skin of the patient
   (b) inserting the proximal end of the catheter through the incision, into the patient;
   (c) forming a subcutaneous tunnel by a trocar or other suitable instrument; wherein the subcutaneous tunnel having a first end coincident to the incision and a second end, there being a distance between the first end of the tunnel and the second end of the tunnel;
   (d) after the subcutaneous tunnel is completely formed, guiding the distal end of the catheter and at least a portion of the central multi-lumen portion through the subcutaneous tunnel from the first end of the subcutaneous tunnel to the second end of the subcutaneous tunnel such that at least a portion of the distal end portion extends outwardly from the second end of the tunnel.

11. The method of claim 10 wherein the single-lumen catheters of the distal end portion are joined together proximate a distal end of each when the distal end of each is guided through the subcutaneous tunnel.

12. The method of claim 11 wherein the distal ends of the distal end single-lumen catheters are joined together by a connector.

13. The method of claim 11 wherein the step of guiding the distal end of the catheter and at least a portion of the central multi-lumen portion of the catheter through the subcutaneous tunnel further comprises the steps of:
   (a) attaching an attachment end of a trocar to the distal end of the catheter; and
   (b) passing the attachment end of the trocar, with the distal end of the catheter attached, through the subcutaneous tunnel.

14. The method of claim 13 wherein a distal end of each of the distal end single-lumen catheters are joined together by the attachment end of the trocar.

15. The method of claim 13 wherein a distal end of each of the distal end single-lumen catheters are joined together by a connector element.

16. The method of claim 13 further comprising placing a sheath having a smooth outer contour over the attachment end of the trocar where it attaches to the distal end of the catheter.

17. A method according to claim 10, the method further comprising connecting one single-lumen catheter of the distal end of the catheter to an arterial leg of a fluid exchange device and connecting another of the single-lumen catheter of the distal end of the catheter to a venous leg of a fluid exchange device.

18. A method according to claim 17, wherein the single-lumen catheters comprising the distal end of the catheter are connected to the fluid exchange device utilizing a first connector hub for each single-lumen catheter.

19. The method of claim 10 wherein the catheter further includes a stabilizing cuff affixed to an outer surface of the catheter, the step of guiding the distal end of the catheter and at least a portion of the central multi-lumen portion through the subcutaneous tunnel further comprising placing the stabilizing cuff between the outer surface of the catheter and an interior wall of the subcutaneous tunnel.

20. The method of claim 19 further comprising dilating at least a portion of the subcutaneous tunnel before guiding the distal end of the catheter and at least a portion of the central multi-lumen portion through the subcutaneous tunnel, wherein the dilating step comprises sliding a sheath dilator along a shaft of a trocar longitudinally positioned in the tunnel.

21. The method of claim 20 further comprising seating the stabilizing cuff in a dilated portion of the subcutaneous tunnel.

22. The method of claim 10 wherein the step of guiding the distal end of the catheter and at least a portion of the multi-lumen tube portion through the subcutaneous tunnel further comprises the steps of:

(a) attaching an attachment end of a trocar to the distal end of the catheter; and (b) passing the attachment end of the trocar, with the distal end of the catheter attached, through the subcutaneous tunnel.

23. The method of claim 22 further comprising placing a sheath having a smooth outer contour over the attachment end of the trocar where it attaches to the distal end of the multi-lumen catheter.

* * * * *